United States Patent
Andree et al.

(10) Patent No.: US 6,495,491 B1
(45) Date of Patent: *Dec. 17, 2002

(54) SUBSTITUTED CYANOPHENYL URACILS

(75) Inventors: Roland Andree, Langenfeld (DE); Mark Wilhelm Drewes, Langenfeld (DE); Otto Schallner, Monheim (DE); Markus Dollinger, Leverkusen (DE); Hans-Joachim Santel, Leverkusen (DE); Christoph Erdelen, Leichlingen (DE); Akihiko Yanagi, Tochigi (JP); Toshio Goto, Tochigi (JP)

(73) Assignees: Bayer Aktiengesellschaft, Leverkusen (DE); Nihon Bayer Agrochem K.K., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/973,670
(22) PCT Filed: Jun. 17, 1996
(86) PCT No.: PCT/EP96/02603
§ 371 (c)(1),
(2), (4) Date: Dec. 22, 1997
(87) PCT Pub. No.: WO97/01541
PCT Pub. Date: Jan. 16, 1997

(30) Foreign Application Priority Data

Jun. 29, 1995 (DE) .......................................... 195 23 650
Dec. 19, 1995 (DE) .......................................... 195 47 475

(51) Int. Cl.$^7$ ........................ C07D 239/54; A01N 43/54
(52) U.S. Cl. ........................ 504/243; 504/230; 504/235; 544/219; 544/295; 544/310
(58) Field of Search ..................... 544/309, 310, 544/313, 180, 182, 219, 295; 504/243, 229, 230, 235

(56) References Cited

U.S. PATENT DOCUMENTS

| | | | | |
|---|---|---|---|---|
| 4,812,164 A | * | 3/1989 | Wenger et al. | 544/312 |
| 4,859,229 A | * | 8/1989 | Wenger et al. | 71/92 |
| 5,084,084 A | * | 1/1992 | Satow et al. | 71/92 |

FOREIGN PATENT DOCUMENTS

| | | | |
|---|---|---|---|
| EP | 255047 | * | 2/1988 |
| EP | 260621 | * | 3/1988 |
| EP | 408382 | * | 1/1991 |
| WO | 95/32952 | * | 12/1995 |
| WO | 96/24590 | * | 8/1996 |

* cited by examiner

Primary Examiner—John M. Ford
(74) Attorney, Agent, or Firm—Norris McLaughlin & Marcus

(57) ABSTRACT

The invention relates to novel substituted cyanophenyluracils of the general formula (I)

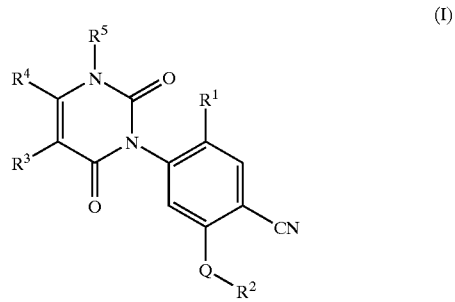

in which $R^1$, $R^2$, $R^3$, $R^4$, $R^5$ and Q are each as defined in the description, to processes for their preparation, to novel intermediates and to their use as herbicides and insecticides.

7 Claims, No Drawings

SUBSTITUTED CYANOPHENYL URACILS

The invention relates to novel substituted cyanophenyluracils, to processes for their preparation and to their use as crop treatment agents, in particular as herbicides and insecticides.

Certain substituted phenyluracils are known to have herbicidal properties (cf. EP-408 382/U.S. Pat. Nos. 5,084,084/5,127,935/5,154,755, EP-563 384, EP-648 749, WO 91/00278, U.S. Pat. Nos. 4,979,982, 5,169,430). However, these compounds have hitherto not attained any major importance.

This invention provides the novel substituted cyanophenyluracils of the general formula (I)

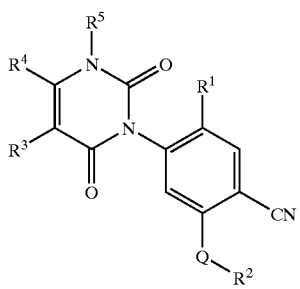

(I)

in which

Q represents O, S, SO or SO$_2$,

R$^1$ represents hydrogen, cyano or halogen,

R$^2$ represents hydrogen or represents a respectively optionally substituted radical from the group consisting of alkyl, alkenyl, alkinyl, cycloalkyl, cycloalkylalkyl, aryl, arylalkyl, heterocyclyl and heterocyclylalkyl, R$^3$ represents hydrogen, halogen or represents a respectively optionally substituted radical from the group consisting of alkyl and alkoxy, R$^4$ represents optionally substituted alkyl and R$^5$ represents hydrogen or represents a respectively optionally substituted radical from the group consisting of alkyl, alkoxy, alkenyl and alkinyl, but excluding the known compounds 1-(4-cyano-2-fluoro-5-methylthio-phenyl)-3,6-dihydro-2,6-dioxo-3-methyl-4-trifluoromethyl-1(2H)-pyrimidine, 1-(4-cyano-2-fluoro-5-methoxycarbonylmethylthio-phenyl)-3,6-dihydro-2,6-dioxo-3-methyl-4-trifluoromethyl-1(2H)-pyrimidine and 1-[4-cyano-2-fluoro-5-(1-ethoxycarbonyl-ethylthio)-phenyl]-3,6-dihydro-2,6-dioxo-3-methyl-4-trifluoromethyl-1(2H)-pyrimidine (cf EP-408 382, p. 85 and U.S. Pat. No. 5,084,084, Col. 76) by disclaimer.

The novel substituted cyanophenyluracils of the general formula (I) are obtained when (a) substituted halogenophenyluracils of the general formula (II)

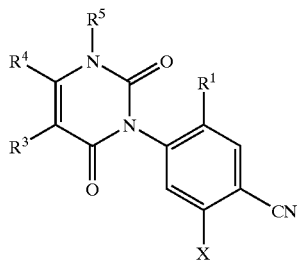

(II)

in which

R$^1$, R$^3$, R$^4$ and R$^5$ are each as defined above and

X represents halogen, are reacted with nucleophilic compounds of the general formula (III)

M—Q—R$^2$ (III)

in which

Q and R$^2$ are each as defined above and

M represents hydrogen or an alkali metal, if appropriate in the presence of a reaction auxiliary and if appropriate in the presence of a diluent, or (b) substituted cyanophenyluracils of the general formula (Ia)

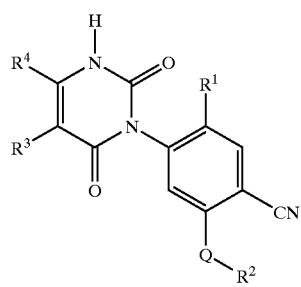

(Ia)

in which

Q, R$^1$, R$^2$, R$^3$ and R$^4$ are each as defined above are reacted with an alkylating agent, if appropriate in the presence of a reaction auxiliary and if appropriate in the presence of a diluent.

The novel substituted cyanophenyluracils of the general formula (I) have strong herbicidal and insecticidal activity.

In the definitions, the saturated or unsaturated hydrocarbon chains, such as alkyl, alkenyl or alkinyl, are in each case straight-chain or branched.

Halogen generally represents fluorine, chlorine, bromine or iodine, preferably flurorine, chlorine or bromine, in particular fluorine or chlorine.

The invention preferably provides compounds of the formula (I)

in which

Q represents O, S, SO or SO$_2$,

R$^1$ represents hydrogen, cyano, fluorine or chlorine,

R$^2$ represents hydrogen, represents respectively optionally cyano-, carboxyl-, fluorine-, chlorine-, bromine-, C$_1$–C$_4$-alkoxy-, C$_1$–C$_4$-alkyl-carbonyl-, C$_1$–C$_4$-alkoxy-carbonyl-, di-(C$_1$–C$_4$-alkyl)-amino-carbonyl- or N—C$_1$–C$_4$-alkyl-N-phenyl-amino-carbonyl- (where the phenyl group is optionally substituted by fluorine, chlorine, bromine, cyano, nitro, methyl or methoxy) substituted alkyl, alkenyl or alkinyl having in each case up to 10 carbon atoms, represents. respectively optionally cyano-, carboxyl-, fluorine-, chlorine-, bromine-, C$_1$–C$_4$-alkyl-, C$_1$–C$_4$-alkoxy-, C$_1$–C$_4$-alkyl-carbonyl- or C$_1$–C$_4$-alkoxy-carbonyl-substituted cycloalkyl or cycloalkylalkyl having 3 to 8 carbon atoms in the cycloalkyl moiety and optionally up to 4 carbon atoms in the alkyl moiety, represents respectively optionally cyano-, carboxyl-, nitro-, carbamoyl-, thiocarbomyl-, fluorine-, chlorine-, bromine-, or C$_1$–C$_4$-alkyl-, C$_1$–C$_4$-alkoxy-, C$_1$–C$_4$-alkylthio-, C$_1$–C$_4$-alkylsulphinyl-, C$_1$–C$_4$-alkyl-sulphonyl-, C$_1$–C$_4$-alkyl-carbonyl- or C$_1$–C$_4$-alkoxy-carbonyl- (each of which is optionally by fluorine and/or chlorine), or phenyl-, phenoxy- or phenylthio- (each of which is optionally substituted by fluorine, chlorine, bromine, cyano, methyl, methoxy, trifluoromethyl and/or trifluoromethoxy) substituted aryl or arylalkyl having 6 or 10 carbon atoms in the aryl moiety and optionally up to 4 carbon atoms in the alkyl moiety, $R^2$ furthermore represents respectively optionally cyano-, carboxyl-, carbamoyl-, thiocarbamoyl-, fluorine-, chlorine-, bromine-, or $C_1$–$C_4$-alkyl, $C_1$–$C_4$-alkoxy-, $C_1$–$C_4$-alkylthio-, $C_1$–$C_4$-alkylsulphinyl-, $C_1$–$C_4$-alkylsulphonyl-, $C_1$–$C_4$-alkyl-carbonyl- or $C_1$–$C_4$-alkoxy-carbonyl- (each of which is optionally by fluorine and/or chlorine), or phenyl-, phenoxy- or phenylthio- (each of which is optionally substituted by fluorine, chlorine, bromine, cyano, methyl, methoxy, trifluoromethyl and/or trifluoromethoxy) substituted substituted furyl, tetrahydrofuryl, thienyl, tetrahydrothienyl, oxetanyl, thietanyl, oxazolyl, isoxazolyl, thiazolyl, oxadiazolyl, thiadiazolyl, pyrazolyl, pyridinyl, pyrimidinyl, triazinyl, indolyl, quinolinyl or quinoxalinyl, $R^3$ represents hydrogen, fluorine, chlorine, bromine or represents respectively optionally fluorine- and/or chlorine-substituted alkyl or alkoxy having in each case 1 to 4 carbon atoms, $R^4$ represents optionally fluorine- and/or chlorine-substituted alkyl having 1 to 4 carbon atoms and $R^5$ represents hydrogen or represents respectively optionally fluorine-, chlorine- or $C_1$–$C_4$-alkoxy-substituted alkyl, alkoxy, alkenyl or alkinyl having in each case up to 6 carbon atoms, but excluding the known compounds 1-(4-cyano-2-fluoro-5-methylthio-phenyl)-3,6-dihydro-2,6-dioxo-3-methyl-4-trifluoromethyl-1(2H)-pyrimidine, 1-(4-cyano-2-fluoro-5-methoxycarbonylmethylthio-phenyl)-3,6-dihydro-2,6-dioxo-3-methyl-4-trifluoromethyl-1(2H)-pyrimidine and 1-[4-cyano-2-fluoro-5-(1-ethoxycarbonyl-ethylthio)-phenyl]-3,6-dihydro-2,6-dioxo-3-methyl-4-trifluoromethyl-1(2H)-pyrimidine (cf. EP-408 382, p. 85 and U.S. Pat No. 5,084,084, Col. 76) by disclaimer.

The invention in particular provides compounds of the formula (I) in which

Q represents O, S, SO or $SO_2$, $R^1$ represents hydrogen, fluorine or chlorine, $R^2$ represents hydrogen, represents respectively optionally cyano-, carboxyl-, fluorine-, chlorine-, methoxy-, ethoxy-, n- or i-propoxy-, acetyl-, propionyl-, methoxycarbonyl-, ethoxycarbonyl-, n- or i-propoxycarbonyl-, dimethylaminocarbonyl- or diethylaminocarbonyl-substituted methyl, ethyl, n- or i-propyl, n-, i-, s- or t-butyl, n-, i-, s- or t-pentyl, propenyl, butenyl, pentenyl, propinyl, butinyl or pentinyl, $R^2$ furthermore represents respectively optionally cyano-, carboxyl-, fluorine-, chlorine-, bromine-, methyl-, ethyl-, n- or i-propyl-, methoxy-, ethoxy-, n- or i-propoxy-, acetyl- or propionyl-, methoxycarbonyl-, ethoxycarbonyl-, n- or i-propoxycarbonyl-substituted cyclopropyl, cyclobutyl, cyclopentyl, cyclohexyl, cyclopropylmethyl, cyclobutylmethyl, cyclopentylmethyl or cyclohexylmethyl, $R^2$ furthermore represents respectively optionally cyano-, carboxyl-, nitro-, carbamoyl-, thiocarbamoyl-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, methylthio-, ethylthio-, methylsulphinyl-, ethylsulphinyl-, methylsulphonyl-, ethylsulphonyl-, acetyl-, propionyl-, methoxycarbonyl-, ethoxycarbonyl-, n- or i-propoxycarbonyl-substituted phenyl, benzyl or phenylethyl, or $R^2$ furthermore represents respectively optionally cyano-, carboxyl-, carbamoyl-, thiocarbamoyl-, fluorine-, chlorine-, bromine-, methyl-, ethyl-, n- or i-propyl-, methoxy-, ethoxy-, n- or i-propoxy-, methylthio-, ethylthio-, methylsulphinyl-, ethylsulphinyl-, methylsulphonyl-, ethylsulphonyl-, acetyl-, propionyl-, methoxycarbonyl-, ethoxycarbonyl-, n- or i-propoxycarbonyl-, or phenyl-, phenoxy- or phenylthio-substituted substituted furyl, tetrahydrofuryl, thienyl, tetrahydrothienyl, oxetanyl, thietanyl, oxazolyl, isoxazolyl, thiazolyl, oxadiazolyl, thiadiazolyl, pyrazolyl, pyridinyl, pyrimidinyl, triazinyl, indolyl, quinolinyl or quinoxalinyl, $R^3$ represents hydrogen, fluorine, chlorine, bromine or methyl, $R^4$ represents methyl, ethyl, difluoromethyl, dichloromethyl, trifluoromethyl, trichloromethyl, chlorodifluoromethyl, fluorodichloromethyl, chloroethyl, fluoroethyl, dichloroethyl, dichloroethyl, chlorofluoroethyl, chlorodifluoroethyl, fluorodichloroethyl, trifluoroethyl, tetrafluoroethyl, chlorotrifluoroethyl or pentafluoroethyl and $R^5$ represents hydrogen or represents respectively optionally fluorine-, chlorine-, methoxy- or ethoxy-substituted methyl, ethyl, n- or i-propyl, n-, i-, s- or t-butyl, methoxy, ethoxy, n- or i-propoxy, n-, i- or s-butoxy, propenyl, butenyl, propinyl or butinyl, but excluding the known compounds 1-(4-cyano-2-fluoro-5-methylthio-phenyl)-3,6-dihydro-2,6-dioxo-3-methyl-4-trifluoromethyl-1(2H)-pyrimidine, 1-(4-cyano-2-fluoro-5-methoxycarbonylmethylthio-phenyl)-3,6-dihydro-2,6-dioxo-3-methyl-4-trifluoromethyl-1(2H)-pyrimidine and 1-[4-cyano-2-fluoro-5-(1-ethoxycarbonyl-ethylthio)-phenyl]-3,6-dihydro-2,6-dioxo-3-methyl-4-trifluoromethyl-1(2H)-pyrimidine (cf. EP-408 382, p. 85 and U.S. Pat. No. 5,084,084, Col. 76) by disclaimer.

The general or preferred radical definitions listed above are valid both for the end products of the formula (I) and also, in a corresponding manner, for starting materials or intermediates which are required in each case for the preparation. These radical definitions can be combined with each other at will, i.e. combinations between the given preferred ranges are also possible.

Examples of the compounds of the formula (I) according to the invention are listed in the groups below.

Group 1

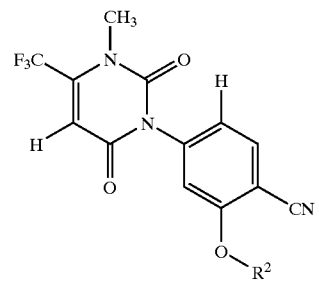

$R^2$ has, for example, the meanings in the list below:

hydrogen, methyl, ethyl, n- or i-propyl, n-, i-, s- or t-butyl, n-, i-, s- or t-pentyl, difluoromethyl, trifluoromethyl, chlorodifluoromethyl, fluorodichloromethyl, fluoroethyl, chloroethyl, chlorofluoroethyl, difluoroethyl, dichloroethyl, trifluoroethyl, trichloroethyl, chlorodifluoroethyl, tetrafluoroethyl, chlorotrifluoroethyl, pentafluoroethyl, fluoropropyl, chloropropyl, difluoropropyl, dichloropropyl, trifluoropropyl, trichloropropyl, cyanomethyl, cyanoethyl, cyanopropyl, cyanobutyl, carboxymethyl, carboxyethyl, carboxypropyl, carboxybutyl, methoxymethyl, ethoxymethyl, propoxymethyl, methoxyethyl, ethoxyethyl, propoxyethyl, methoxypropyl, ethoxypropyl, propoxypropyl, methoxycarbonylmethyl, ethoxycarbonylmethyl, propoxycarbonylmethyl, methoxycarbonylethyl, ethoxycarbonylethyl, propoxycarbonylethyl, methoxycarbonylpropyl, ethoxycarbonylpropyl, propoxycarbonylpropyl, 1-propen-3-yl (allyl), 3-methyl-1-propen-3-yl, 2-buten-4-yl (crotonyl), 1-propin-3-yl (propargyl), 3-methyl-1-propin-3-yl, 2-butin-4-yl, cyclopropyl, cyanocyclopropyl, carboxycyclopropyl, difluorocyclopropyl, dichlorocyclopropyl, methylcyclopropyl, methoxycarbonylcyclopropyl, ethoxycarbonylcyclopropyl, cyclobutyl, cyanocyclobutyl, carboxycyclobutyl, difluorocyclopropyl, trifluorocyclobutyl, tetrafluorocyclobutyl, chlorotrifluorocyclobutyl, methylcyclobutyl, cyclopentyl, cyanocyclopentyl, carboxycyclopentyl, fluorocyclopentyl, chlorocyclopentyl, difluorocyclopentyl, dichlorocyclopentyl, methylcyclopentyl, methoxycarbonylcyclopentyl, ethoxycarbonylcyclopentyl, cyclohexyl, cyanocyclohexyl, carboxycyclohexyl, fluorocyclohexyl, chlorocyclohexyl, difluorocyclohexyl, dichlorocyclohexyl, methylcyclohexyl, trifluoromethylcyclohexyl, methoxycarbonylcyclohexyl, ethoxycarbonylcyclohexyl, cyclopropylmethyl, difluorocyclopropylmethyl, dichlorocyclopropylmethyl, cyclobutylmethyl, cyclopentylmethyl, cyclohexylmethyl, cyanocyclohexylmethyl, carboxycyclohexylmethyl, fluorocyclohexylmethyl, chlorocyclo-hexylmethyl, methylcyclohexylmethyl, trifluoromethylcyclohexylmethyl, phenyl, cyanophenyl, carboxyphenyl, nitrophenyl, fluorophenyl, chlorophenyl, bromophenyl, methylphenyl, trifluoromethylphenyl, methoxyphenyl, difluoromethoxyphenyl, trifluoromethoxyphenyl, methoxycarbonylphenyl, ethoxycarbonylphenyl, benzyl, cyanobenzyl, carboxybenzyl, fluorobenzyl, chlorobenzyl, methylbenzyl, trifluoromethylbenzyl, methoxybenzyl, difluoromethoxybenzyl, trifluoromethoxybenzyl, methoxycarbonylbenzyl, ethoxycarbonylbenzyl, phenylethyl, furyl, tetrahydrofuryl, thienyl, tetrahydrothienyl, oxetanyl, oxazolyl, isoxazolyl.

Group 2

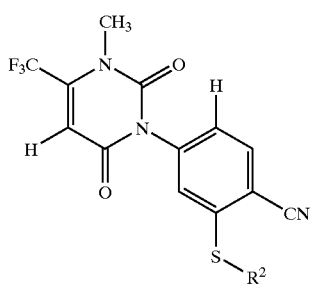

$R^2$ has, for example, the meanings listed above in Group 1.

Group 3

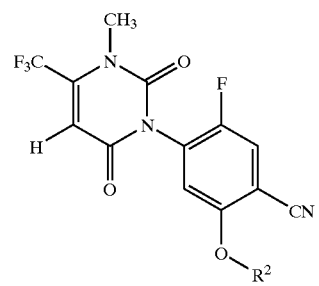

$R^2$ has, for example, the meanings listed above in Group 1.

Group 4

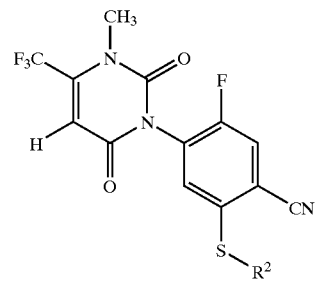

$R^2$ has, for example, the meanings listed above in Group 1.

Group 5

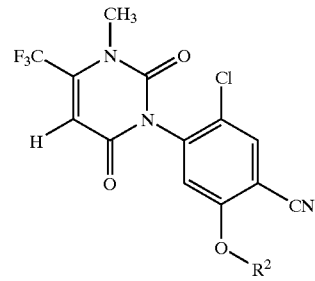

$R^2$ has, for example, the meanings listed above in Group 1.

Group 6

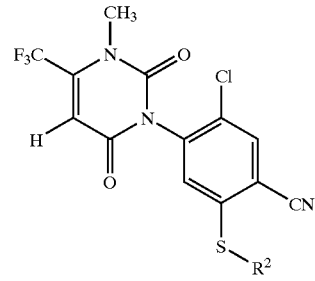

$R^2$ has, for example, the meanings listed above in Group 1.

Group 7

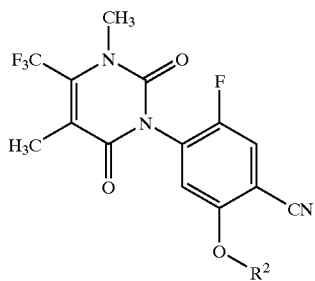

$R^2$ has, for example, the meanings listed above in Group 1.

Group 8

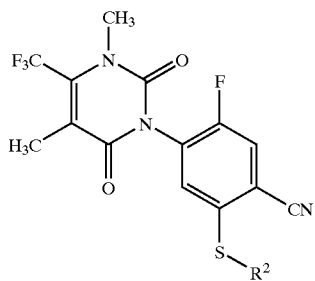

$R^2$ has, for example, the meanings listed above in Group 1.

Group 9

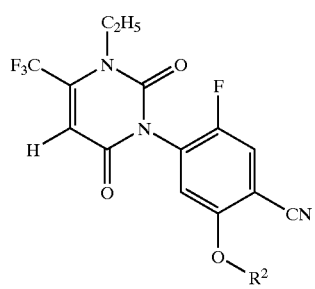

$R^2$ has, for example, the meanings listed above in Group 1.

Group 10

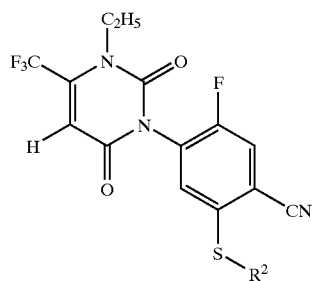

$R^2$ has, for example, the meanings listed above in Group 1.

Group 11

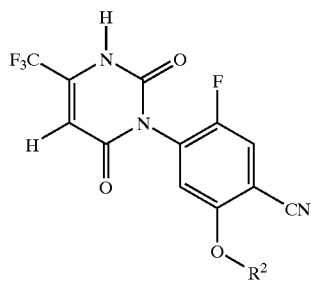

$R^2$ has, for example, the meanings listed above in Group 1.

Group 12

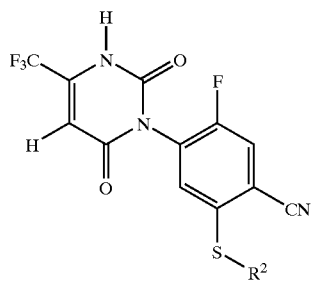

$R^2$ has, for example, the meanings listed above in Group 1.

Group 13

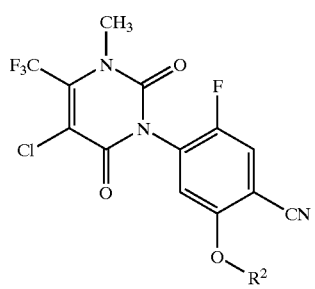

$R^2$ has, for example, the meanings listed above in Group 1.

Group 14

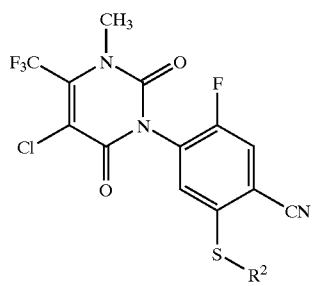

$R^2$ has, for example, the meanings listed above in Group 1.

Group 15

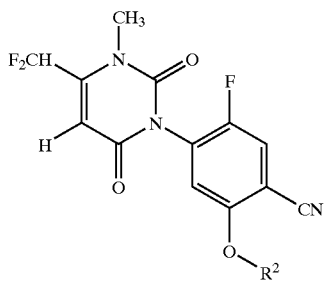

$R^2$ has, for example, the meanings listed above in Group 1.

Group 16

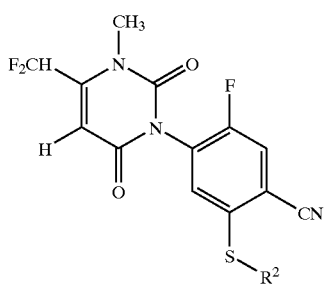

$R^2$ has, for example, the meanings listed above in Group 1.

Group 17

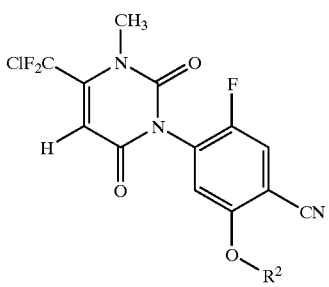

$R^2$ has, for example, the meanings listed above in Group 1.

Group 18

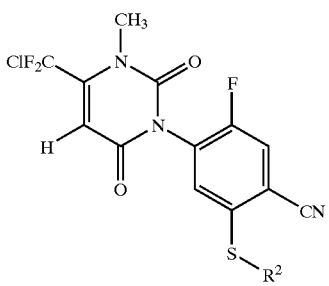

$R^2$ has, for example, the meanings listed above in Group 1.

Group 19

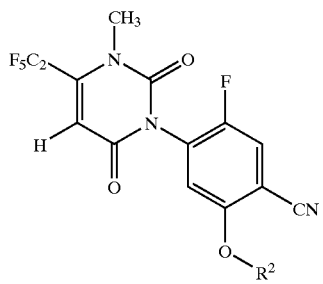

$R^2$ has, for example, the meanings listed above in Group 1.

Group 20

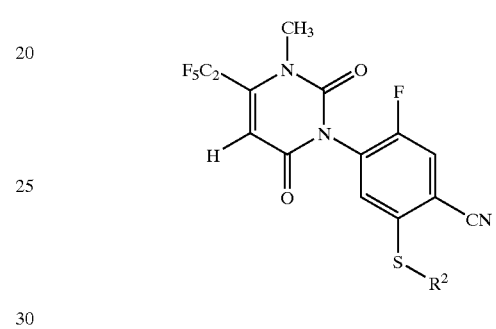

$R^2$ has, for example, the meanings listed above in Group 1.

Using, for example, 1-(4-cyano-2,5-difluoro-phenyl)-3,6-dihydro-2,6-dioxo-5-chloro-4-difluoromethyl-3-methyl-1 (2H)-pyrimidine and potassium ethoxide as starting materials, the course of the reaction in the process (a) according to the invention can be illustrated by the following scheme:

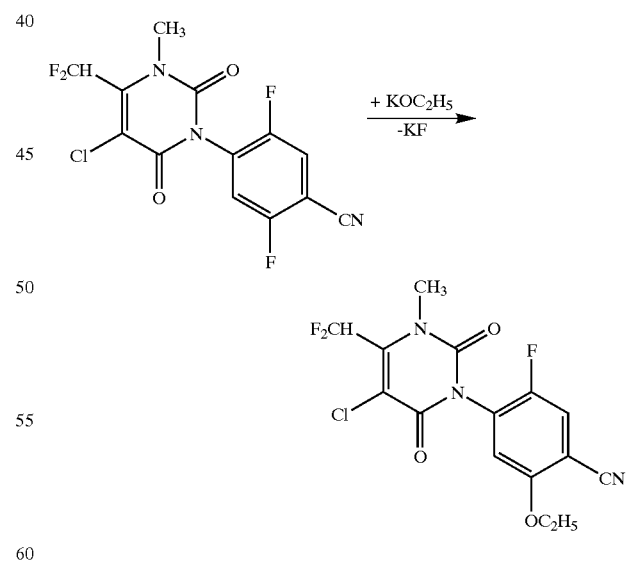

Using, for example, 1-(2-chloro-4-cyano-5-methylthio-phenyl)-3,6-dihydro-2,6-dioxo-4-chlorodifluoromethyl-5-methyl-1(2H)-pyrimidine and bromomethane as starting materials, the course of the reaction in the process (b) according to the invention can be illustrated by the following scheme:

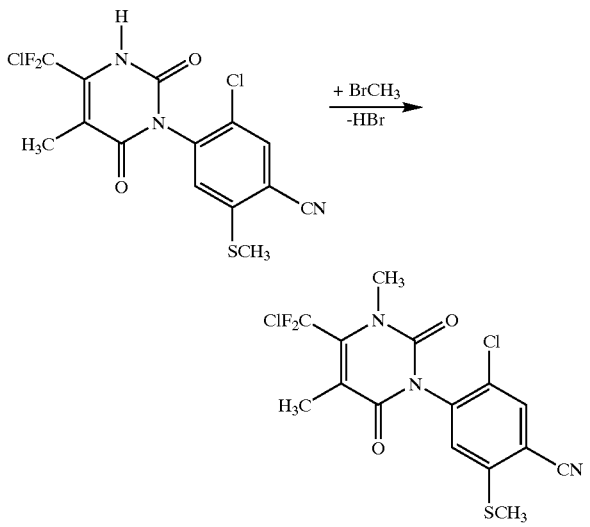

The formula (II) provides a general definition of the substituted halogenophenyluracils to be used as starting materials in the process according to the invention for preparing the compounds of the formula (I). In the formula (II), $R^1$, $R^3$, $R^4$ and $R^5$ each preferably or in particular have that meaning which has already been indicated above, in the description of the compounds of the formula (I) to be prepared according to the invention, as preferred or as particularly preferred for $R^1$, $R^3$, $R^4$ and $R^5$; X preferably represents fluorine, chlorine or bromine, in particular fluorine.

The starting materials of the formula (II) are known and/or can be prepared by processes known per se (EP 648749, Preparation Examples).

The formula (III) provides a general definition of the nucleophilic compounds further to be used as starting materials in the process according to the invention for preparing the compounds of the formula (I). In the formula (III), Q and $R^2$ each preferably or in particular have that meaning which has already been indicated above,. in the description of the compounds of the formula (I) to be prepared according to the invention, as preferred or as particularly preferred for Q and $R^2$; M preferably represents hydrogen, lithium,. sodium or potassium, in particular hydrogen, sodium or potassium.

The starting materials of the formula (III) are known chemicals for synthesis.

The process (a) according to the invention for preparing the compounds of the formula (I) is preferably carried out in the presence of a suitable reaction auxiliary. Suitable reaction auxiliaries are generally the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2,2,2]-octane (DABCO), 1,5-diazabicyclo[4,3,0]-non-5-ene (DBN), and 1,8-diazabicyclo[5,4,0]-undec-7-ene (DBU).

The process (a) according to the invention for preparing the compounds of the formula (I) is preferably carried out in the presence of a diluent. Suitable diluents are generally the customary organic solvents. These preferably include aliphatic, alicyclic and aromatic, optionally halogenated hydrocarbons, such as, for example, pentane, hexane, heptane, petroleum ether, ligroin, benzine, benzene, toluene, xylene, chlorobenzene, dichlorobenzene, cyclohexane, methylcyclohexane, di-chloromethane (methylene chloride), trichloromethane (chloroform) or carbon tetrachloride, dialkyl ethers, such as, for example, diethyl ether, diisopropyl ether, methyl-t-butyl ether (MTBE), ethyl-t-butyl ether, methyl-t-pentyl ether (TAME), ethyl-t-pentyl ether, tetrahydrofuran (THF), 1,4-dioxane, ethylene glycol dimethyl ether or ethylene glycol diethyl ether, diethylene glycol dimethyl ether or diethylene glycol diethyl ether; dialkyl ketones, such as, for example, acetone, butanone (methyl ethyl ketone), methyl-i-propyl ketone or methyl-i-butyl ketone, nitriles, such as, for example acetonitrile, propionitrile, butyronitrile or benzonitrile; amides, such as, for example, N,N-dimethyl-formamide (DMF), N,N-dimethyl-acetamide, N-methyl-formamide, N-methyl-pyrrolidone or hexamethyl-phosphoric triamide; esters, such as, for example, methyl acetate, ethyl acetate, n- or i-propyl acetate, n-, i- or s-butyl acetate; sulphoxides, such as, for example, dimethyl sulphoxide; alcohols, such as, for example, methanol, ethanol, n- or i-propanol, n-, i-, s- or t-butanol, ethylene glycol monomethyl ether or ethylene glycol monoethyl ether, diethylene glycol monomethyl ether or diethylene glycol monoethyl ether; mixtures thereof with water or pure water.

When carrying out the process (a) according to the invention, the reaction temperatures can be varied over a relatively wide range. In general, temperatures of between 0° C. and 200° C., preferably between 10° C. and 150° C., are employed.

The process (a) according to the invention is generally carried out under atmospheric pressure. However, it is also possible to carry out the process according to the invention under elevated or reduced pressure—in general between 0.1 bar and 10 bar.

To carry out the process (a) according to the invention, the starting materials are generally employed in approximately equimolar amounts. However, it is also possible to use one of the components in a relatively large excess. The reaction is generally carried out in a suitable diluent in the presence of a reaction auxiliary, and the reaction mixture is generally stirred for several hours at the temperature required. Work-up is carried out according to customary methods (cf. the Preparation Examples).

The formula (Ia) provides a general definition of the substituted cyanophenyluracils to be used as starting materials in the process (b) according to the invention for preparing the compounds of the formula (I). In the formula (Ia), Q, $R^1$, $R^2$, $R^3$ and $R^4$ each preferably or in particular have that meaning which has already been indicated above, in the description of the compounds of the formula (I) to be prepared according to the invention, as preferred or as particularly preferred for Q, $R^1$, $R^2$, $R^3$ and $R^4$.

The starting materials of the formula (Ia) are novel compounds according to the invention; they can be prepared by the process (a) according to the invention.

The process (b) according to the invention is carried out using an alkylating agent. Alkylating agents in this context are preferably optionally fluorine-, chlorine- or $C_1$–$C_4$-alkoxy-substituted alkyl halides, alkenyl halides or alkinyl halides (in particular chlorides, bromides or iodides) having in each case up to 6 carbon atoms, or dialkyl sulphates having up to 6 carbon atoms in the alkyl groups. The compounds are known chemicals for synthesis.

The process (b) according to the invention for preparing the compounds of the formula (I) is preferably carried out in the presence of a suitable reaction auxiliary. Suitable reaction auxiliaries are generally the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide or potassium methoxide, sodium ethoxide or potassium ethoxide, sodium n- or i-propoxide or potassium n- or i-propoxide, sodium n-, i-, s- or t-butoxide or potassium n-, i-, s- or t-butoxide; furthermore also basic organic nitrogen compounds, such as, for example, trimethyl amine, tri ethyl amine, tripropylamine, tributyl amine, ethyl-diisopropylamine, N,N-dimethyl-cyclohexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethylpyridine, 5-ethyl-2-methyl-pyridine, 4-dimethylamino-pyridine, N-methylpiperidine, 1,4-diazabicyclo[2,2,2]-octane (DABCO), 1,5-diazabicyclo[4,3,0]-non-5-ene (DBN), or 1,8-diazabicyclo[5,4,0]-undec-7-ene (DBU).

The process (b) according to the invention for preparing the compounds of the formula (I) is preferably carried out in the presence of a diluent. Suitable diluents are generally the customary organic solvents. These preferably include aliphatic, alicyclic and aromatic, optionally halogenated hydrocarbons, such as, for example, pentane, hexane, heptane, petroleum ether, ligroin, benzine, benzene, toluene, xylene, chlorobenzene, dichlorobenzene, cyclohexane, methylcyclohexane, dichloromethane (methylene chloride), trichloromethane (chloroform) or tetrachloromethane, dialkyl ethers, such as, for example, diethyl ether, diisopropyl ether, methyl t-butyl ether (MTBE), ethyl t-butyl ether, methyl t-pentyl ether (TAME), ethyl t-pentyl ether, tetrahydrofuran (THF), 1,4-dioxane, ethylene glycol dimethyl ether or ethylene glycol diethyl ether, diethylene glycol dimethyl ether or diethylene glycol diethyl ether; dialkyl ketones, such as, for example, acetone, butanone (methyl ethyl ketone), methyl i-propyl ketone or methyl i-butyl ketone, nitriles, such as, for example, acetonitrile, propionitrile, butyronitrile or benzonitrile; amides, such as, for example, N,N-dimethyl-formamide (DMF), N,N-dimethyl-acetamide, N-methyl-formanilide, N-methyl-pyrrolidone or hexamethylphosphoric triamide; esters, such as, for example, methyl acetate, ethyl acetate, n- or i-propyl acetate, n-, i- or s-butyl acetate; sulphoxides, such as, for example, dimethyl sulphoxide; alkanols, such as, for example, methanol, ethanol, n- or i-propanol, n-, i-, s- or t-butanol, ethylene glycol monomethyl ether or ethylene glycol monoethyl ether, diethylene glycol monomethyl ether or diethylene glycol monoethyl ether; mixtures thereof with water or pure water.

When carrying out the process (b) according to the invention, the reaction temperatures can be varied over a relatively wide range. In general, temperatures of between 0° C. and 150° C., preferably between 10° C. and 120° C., are employed.

The process (b) according to the invention is generally carried out under atmospheric pressure. However, it is also possible to carry out the process according to the invention under elevated or reduced pressure—in general between 0.1 bar and 10 bar.

To carry out the process (b) according to the invention, the starting materials are generally employed in approximately equimolar amounts. However, it is also possible to use one of the components in a relatively large excess. The reaction is generally carried out in a suitable diluent in the presence of a reaction auxiliary, and the reaction mixture is generally stirred for several hours at the temperature required. Work-up is carried out according to customary methods (cf. the Preparation Examples).

The active compounds according to the invention can be used as defoliants, desiccants, haulm-killers and, especially, as weed-killers. By weeds, in the broadest sense, are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cycnodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total control of weeds, for example on industrial terrain and rail tracks, and on paths and squares with or without tree plantings. Equally, the compounds can be employed for controlling weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, on lawns, turf and pasture-land, and for the selective control of weeds in annual crops.

The compounds of the formula (I) according to the invention are particularly suitable for the selective control of monocotyledonous and dicotyledonous weeds in monocotyledonous or dicotyledenous crops by both the pre- and the post-emergence method.

Furthermore, the compounds of the formula (I) according to the invention also have strong insecticidal activity, especially against beetle larvae, such as, for example, *Phaedon cochleariae*, and against the caterpillars of butterflies, such as, for example, *Plutella xylostella*.

To a certain extent, the compounds of the formula (I) also exhibit fungicidal activity, for example against *Pyricularia oryzae* in rice.

The active compounds, having good crop tolerance and homeotherm safety, are suitable for controlling animal pests, in particular insects, arachnids and nematodes, which are encountered in agriculture, in forestry, in the protection of stored products and of materials, and in the hygiene sector. They are preferably used as crop protection agents. They are active against normally sensitive and resistant species and against all or some stages of development. The abovementioned pests include:

From the order of Isopoda, for example, *Oniscus asellus, Armadillidium vulgare* and *Porcellio scaber.*

From the order of the Diplopoda, for example, *Blaniulus guttulatus*. From the order of the Chilopoda, for example, *Geophilus carpophagus* and *Scutigera spec. From the order of the Symphyla, for example, Scutigerella immaculata.*

From the order of the Thysanura, for example, *Lepisma saccharina*. From the order of the Collembola, for example, *Onychiurus armatus*.

From the order of the Orthoptera, for example, *Blatta orientalis, Periplaneta americana, Leucophaea maderae, Blatella germanica, Acheta domesticus,* Gryllotalpa spp., *Locusta-migratoria* migratorioides, Melanoplus differentialis and *Schistocerca gregaria*.

From the order of the Dermaptera, for example, *Forficula auricularia*. From the order of the Isoptera, for example, Reticulitermes spp. From the order of the Anoplura, for example, *Pediculus humanus corporis*, Haematopinus spp. and Linognathus spp.

From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix,* Pemphigus spp., *Macrosiphum avenae,* Myzus spp., *Phorodon humuli; Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.

From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella,*

*Phyllocnistis citrella,* Agrotis spp., Euxoa spp., Feltia spp., *Earias insulana,* Heliothis spp., *Spodoptera exigua, Mamestra brassicae, Panolis flammea, Spodoptera litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana*.

From the order of the Coleoptera, for example, *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon soistitialis,* and *Costelytra zealandica*.

From the order of the Hymenoptera, for example, Diprion spp., Hoplocampa spp., Lasius spp., *Monomorium pharaonis* and Vespa spp.

From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa*.

From the order of the Siphonaptera, for example, *Xenopsylla cheopis* and Ceratophyllus spp.

From the order of the Arachnida, for example, *Scorpio maurus* and *Latrodectus mactans*.

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include, for example, Pratylenchus spp., *Radopholus similis, Ditylenchus dipsaci, Tylenchulus semipenetrans,* Heterodera spp., Globodera spp., Meloidogyne spp., Aphelenchoides spp., Longidorus spp., Xiphinema spp., Trichodorus spp.

Suitable compounds are, for example, those listed below:
Fungicides
2-aminobutane; 2-anilino-4-methyl-6-cyclopropyl-pyrimidine; 2',6'-dibromo-2-methyl-4'-trifluoromethoxy-4'-trifluoro-methyl-1,3-thiazole-5-carboxanilide; 2,6-dichloroN-(4-trifluoromethylbenzyl)-benzamide; (E)-2-methoxyimino-N-methyl-2-(2-phenoxyphenyl)-acetamide; 8-hydroxyquinoline sulphate; methyl (E)-2-{2-[6-(2-cyanophenoxy)-pyrimidin-4-yloxy]-phenyl}-3-methoxyacrylate; methyl (E)-methoximino-[alpha-(o-tolyloxy)-o-tolyl]-acetate; 2-phenylphenol (OPP), aldimorph, ampropylfos, anilazine, azaconazole, benalaxyl, benodanil, benomyl, binapacryl, biphenyl, bitertanol, blasticidin-S, bromuconazole, bupirimate, buthiobate, calcium polysulphide, captafol, captan, carbendazim, carboxin, quinomethionate, chloroneb, chloropicrin, chlorothalonil, chlozolinate, cufraneb, cymoxanil, cyproconazole, cyprofuram, dichlorophen, diclobutrazol, diclofluanid, diclomezin, dicloran, diethofencarb, difenoconazole, dimethirimol, dimethomorph, diniconazole, dinocap, diphenylamine, dipyrithion, ditalimfos, dithianon, dodine, drazoxolon, edifenphos, epoxyconazole, ethirimol, etridiazole, fenarimol, fenbuconazole, fenfuram, fenitropan, fenpiclonil, fenpropidin, fenpropimorph, fentin acetate, fentin hydroxide, ferbam, ferimzone, fluazinam, fludioxonil, fluoromide, fluquinconazole, flusilazole, flusulphamide, flutolanil, flutriafol, folpet, fosetyl-aluminium, fthalide, fuberidazole, furalaxyl, furmecyclox, guazatine, hexachlorobenzene, hexaconazole, hymexazol, imazalil, imibenconazole, iminoctadine, iprobenfos (IBP), iprodione, isoprothiolane, kasugamycin, copper preparations such as: copper hydroxide, copper naphthenate, copper oxychloride, copper sulphate, copper oxide, oxine-copper and Bordeaux mixture, mancopper, mancozeb, maneb, mepanipyrim, mepronil, metalaxyl, metconazole, methasulphocarb, methfuroxam, metiram, metsulphovax, myclobutanil, nickel dimethyldithiocarbamate, nitrothal-isopropyl, nuarimol; ofurace, oxadixyl, oxamocarb, oxycarboxin, pefurazoate, penconazole, pencycuron; phosdrphen, phthalide, pimaricin, piperalin, polycarbamates, polyoxin, probenazole, prochloraz, proeymidone, propamocarb, propiconazole, propineb, pyrazophos, pyrifenox, pyrimethanyl, pyroquilon, quintozene (PCNB), sulphur and sulphur preparations, tebucanozole, tecloftalam, tecnazene, tetraconazole, thiabendazole, thicyofen, thio-phanate-methyl, thiram, tolclophos-methyl, tolylfluanid, triadimefon, triadimenol, triazoxide, trichlamide, tricyclazole, tridemorph, triflumizole, triforin, triticonazole, validamycin A, vinclozolin, zineb, ziram.

Bactericides bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides abamectin, AC 303 630, acephate, acrinathrin, alanycarb, aldicarb, alphamethrin, amitraz, avermectin, AZ 60541, azadirachtin, azinphos A, azinphos M, azocyclotin. *Bacillus thuringiensis,* bendiocarb, benfuracarb, bensultap, beta-cyfluthrin, bifenthrin, BPMC, brofenprox, bromophos A, bufencarb, buprofezin, butocarboxin, butylpyridaben, cadusafos, carbaryl, carbofuran, carbophenothion, carbosulphan, cartap, CGA 157 419, CGA 184699, chloethocarb, chlorethoxyfos, chlorfenvinphos, chlorfluazuron, chlormephos, chlorpyrifos, chlorpyrifos M, cis-resmethrin, clocythrin, clofentezine, cyanophos, cycloprothrin, cyfluthrin, cyhalothrin, cyhexatin, cypermethrin, cyromazine, deltamethrin, demeton-M, demeton-S, demeton-S-methyl, diafenthiuron, diazinon, dichlofenthion, dichlorvos, dicliphos, dicrotophos, diethion, diflubenzuron, dimethoate, dimethylvinphos, dioxathion, disulphoton, edifenphos, emamectin, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, fluazinam, flucycloxuron, flucythrinate, flufenoxuron, flufenprox, fluvalinate, fonophos, formothion, fosthiazate, fubfenprox, furathiocarb, HCH, heptenophos, hexaflumuron, hexythiazox, imidacloprid, iprobenfos, isazophos, isofenphos, isoprocarb, isoxathion, ivemectin, lambda-cyhalothrin, lufenuron, malathion, mecarbam, mevinphos, mesulphenphos, metaldehyde, methacrifos, methamidophos, methidathion, methiocarb, methomyl, metolcarb, milbemectin, monocrotophos, moxidectin, naled, NC 184, NI 25, nitenpyram, omethoate, oxamyl, oxydemethon M, oxydeprofos, parathion A, parathion M, permethrin, phenthoate, phorate, phosalone, phosmet, phosphamidon, phoxim, pirimicarb, pirimiphos M, pirimiphos A, profenofos, promecarb, propaphos, propoxur, prothiofos, prothoate, pymetrozin, pyrachlophos, pyradaphenthion, pyresmethrin, pyrethrum, pyridaben, pyrimidifen, pyriproxifen, quinalphos, RH 5992, salithion, sebufos, silafluofen, sulphotep, sulprofos, tebufenozid, tebufenpyrad, tebupirimphos, teflubenzuron, tefluthrin, temephos, terbam, terbufos, tetrachlorvinphos, thiafenox, thiodicarb, thiofanox, thiomethon, thionazin, thuringiensin, tralomethrin, triarathen, triazophos, triazuron, trichlorfon, triflumuron, trimethacarb, vamidothion, XMC, xylylcarb, YI 5301/5302, zetamethrin.

A mixture with other known active compounds, such as herbicides, or with fertilizers and growth regulators, is also possible.

The active compounds according to the invention can furthermore be present in their commercially available formulations and in the use forms prepared from these formulations, as a mixture with synergists. Synergists are compounds which increase the action of the active compounds without it being necessary for the synergist added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound has an excellent residual action on wood and clay as well as a good stability to alkali on limed substrates.

The active compounds according to the invention are not only active against plant, hygiene and stored-product pests, but also, in the veterinary medicine sector, against animal parasites (ectoparasites), such as ixodid ticks, argasid ticks, scab mites, trombiculid mites, flies (stinging and sucking), parasitic fly larvae, lice, hair lice, bird lice and fleas. These parasites include:

From the order of the Anoplurida, for example, Haematopinus spp., Linognathus spp., Pediculus spp., Phtirus spp., Solenopotes spp.

From the order of the Mallophagida and the sub-orders Amblycerina and Ischnocerina, for example, Trimenopon spp., Menopon spp., Trinoton spp., Bovicola spp., Werneckiella spp., Lepikentron spp., Damalina spp., Trichodectes spp., Felicola spp.

From the order Diptera and the sub-orders Nematocerina and Brachycerina, for example, Aedes spp., Anopheles spp., Culex spp., Simulium spp., Eusimulium spp., Phlebotomus spp., Lutzomyia spp., Culicoides spp., Chrysops spp., Hybomitra spp., Atylotus spp., Tabanus spp., Haematopota spp., Philipomyia spp., Braula spp., Musca spp., Hydrotaea spp., Stomoxys spp., Haematobia spp., Morellia spp., Fannia spp., Glossina spp., Calliphora spp., Lucilia spp., Chrysomyia spp., Wohlfahrtia spp., Sarcophaga spp., Oestrus spp., Hypoderma spp., Gasterophilus spp., Hippobosca spp., Lipoptena spp. and Melophagus spp., From the order of the Siphonapterida, for example, Pulex spp., Ctenocephalides spp., Xenopsylla spp. and Ceratophyllus spp.

From the order of the Heteropterida, for example, Cimex spp., Triatoma spp., Rhodnius spp. and Panstrongylus spp.

From the order of the Blattarida, for example, *Blatta orientalis, Periplaneta americana, Blattela germanical* and Supella spp.

From the sub-class of the Acaria (Acarida) and the orders of the Meta- and Mesostigmata, for example Argas spp., Ornithodorus spp., Otobius spp., Ixodes spp., Amblyomma spp., Boophilus spp., Dermacentor spp., Haemophysalis spp., Hyalomma spp., Rhipicephalus spp., Dermanyssus spp., Raillietia spp., Pneumonyssus spp., Sternostoma spp. and Varroa spp.

From the order of the Actinedida (Prostigmata) and Acaridida (Astigmata), for example Acarapis spp., Cheyletiella spp., Ornithocheyletia spp., Myobia spp, Psorergates spp., Demodex spp., Trombicula spp., Listrophorus spp., Acarus spp., Tyrophagus spp., Caloglyphus spp., Hypodectes spp., Pterolichus spp., Psoroptes spp., Chorioptes spp., Octodectes spp., Sarcoptes spp., Notoedres spp., Knemidocoptes spp., Cytodites spp. and Laminosioptes spp.

The active compounds of the formula (I) according to the invention are also suitable for controlling arthropods which attack agricultural livestock, such as, for example, cattle, sheep, goats, horses, pigs, donkeys, camels, buffalo, rabbits, chickens, turkeys, ducks, geese, honey bees, other domestic animals, such as, for example, dogs, cats, cage birds, aquarium fish, and so-called experimental animals such as, for example, hamsters, guinea-pigs, rats and mice. By controlling these arthropods, it is intended to reduce mortality and decreased performance (in meat, milk, wool, hides, eggs, honey and the like), so that more economical and simpler animal keeping is made possible by using the active compounds according to the invention.

In the veterinary sector, the active compounds according to the invention are used in a known manner by enteral administration, for example in the form of tablets, capsules, drinks, drenches, granules, pastes, boluses, the feed-through method, suppositories, by parenteral administration, such as, for example, by means of injections (intramuscular, subcutaneous, intravenous, intraperitoneal and the like), implants, by nasal application, by dermal administration, for example in the form of dipping or bathing, spraying, pouring-on and spotting-on, washing, dusting, and with the aid of shaped articles which comprise active compound, such as collars, ear tags, tail marks, limb bands, halters, marking devices and the like.

When administered to livestock, poultry, domestic animals and the like, the active compounds of the formula (I) can be used as formulations (for example powders emulsions, flowables) which comprise the active compounds in an amount of 1 to 80% by weight, either directly or after dilution by a factor of 100 to 10,000, or they may be used in the form of a chemical bath.

Furthermore, it has been found that the compounds of the formula (I) according to the invention have a potent insecticidal action against insects which destroy industrial materials.

The following insects may be mentioned by way of example and as being preferred, but without any limitation.

Beetles, such as *Hylotrupes bajulus, Chlorophorus pilosis, Anobium punctatum, Xestobium rufovillosum, Ptili-nus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis*; Xyleborus spec., Tryptodendron spec., *Apate monachus, Bostrychus capucins, Heterobostrychus brunneus,* Sinoxylon spec., *Dinoderus minutus;*

Dermapterans, such as *Sirex juvencus, Urocerus gigas, Urocerus gigas taignus, Urocerus augur;*

Termites, such as *Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus;*

Bristletails, such as *Lepisma saccharina.*

Industrial materials are to be understood as meaning, in the present context, non-live materials such as, preferably, synthetic materials, glues, sizes, paper and board, leather, wood and timber products, and paint.

The materials to be very particularly protected against attack by insects are wood and timber products.

Wood and timber products which can be protected by the composition according to the invention or mixtures comprising such a composition are to be understood as meaning, for example, construction timber, wooden beams, railway sleepers, bridge components, jetties, wooden vehicles, boxes, pallets, containers, telephone poles, wood lagging, windows and doors made of wood, plywood, particle board, joiner's articles, or wood products which, quite generally, are used in the construction of houses or in joinery.

The active compounds can be used as such, in the form of concentrates or generally customary formulations, such as powders, granules, solutions, suspensions, emulsions or pastes.

The formulations mentioned can be prepared in a manner known per se, for example by mixing the active compounds with at least one solvent or diluent, emulsifier, dispersant and/or binder or fixative, water repellent, if appropriate desiccants and UV stabilizers and, if appropriate, colorants and pigments and other processing auxiliaries.

The insecticidal compositions or concentrates used for the protection of wood and wooden materials comprise the active compound according to the invention at a concentration of 0.0001 to 95% by weight, in particular 0.001 to 60% by weight.

The amount of the compositions or concentrates employed depends on the species and the occurrence of the insects and on the medium. The optimum rate of application can be determined upon use in each case by test series. However, in general, it suffices to employ 0.0001 to 20% by weight, preferably 0.001 to 10% by weight, of the active compound, based on the material to be protected.

The solvent and/or diluent used is an organochemical solvent or solvent mixture and/or an oily or oil-type organochemical solvent or solvent mixture of low volatility and/the a polar organochemical solvent or solvent mixture and/or water and, if appropriate, an emulsifier and/or wetting agent.

Organochemical solvents which are preferably employed are oily or oil-type solvents having an evaporation number of above 35 and a flashpoint of above 30° C., preferably above 45° C. Substances which are used as such oily and oil-type solvents which have low volatility and are insoluble in water are suitable mineral oils or their aromatic fractions, or mineral-oil-containing solvent mixtures, preferably white spirit, petroleum and/or alkylbenzene.

Substances which are advantageously used are mineral oils with a boiling range of 170 to 220° C., white spirit with a boiling range of 170 to 220° C., spindle oil with a boiling range of 250 to 350° C., petroleum or aromatics of boiling range 1–60 to 280° C., essence of turpentine and the like.

In a preferred embodiment, liquid aliphatic hydrocarbons with a boiling range of 180 to 210° C. or high-boiling mixtures of aromatic and aliphatic hydrocarbons with a boiling range of 180 to 220° C. and/or spindle oil and/or monochloro-naphthalene, preferably α-monochloro-naphthalene, are used.

The organic oily or oil-type solvents of low volatility having an evaporation number of above 35 and a flashpoint of above 30° C., preferably above 45° C., can be partially replaced by organochemical solvents of high or medium volatility, with the proviso that the solvent mixture also has an evaporation number of above 35 and a flashpoint of above 30° C., preferably above 45° C., and that the insecticide/fungicide mixture is soluble or emulsifiable in this solvent mixture.

In a preferred embodiment, part of the organochemical solvent or solvent mixture is replaced by an aliphatic polar organochemical solvent or solvent mixture. Substances which are preferably used are aliphatic organochemical solvents having hydroxyl and/or ester and/or ether groups, such as, for example, glycol ether, esters and the like.

The organochemical binders used within the scope of the present invention are the synthetic resins and/or binding drying oils which are known per se and can be diluted with water and/or are soluble or dispersible or emulsifiable in the organochemical solvents employed, in particular binders composed of, or comprising, an acrylate resin, a vinyl resin, for example polyvinyl acetate, polyester resin, polycondensation or polyaddition resin, polyurethane resin, alkyd resin or modified alkyd resin, phenol resin, hydrocarbon resin, such as indene/coumarone resin, silicone resin, drying vegetable and/or drying oils and/or physically drying binders based on a natural and/or synthetic resin.

The synthetic resin used as the binder can be employed in the form of an emulsion, dispersion or solution. Up to 10% by weight of bitumen or bituminous substances can also be used as binders. In addition, known colorants, pigments, water repellents, odour-masking substances and inhibitors or anticorrosives per se and the like can also be employed.

The composition or the concentrate preferably comprises, in accordance with the invention, at least one alkyd resin or modified alkyd resin and/or a drying vegetable oil as the organochemical binder. Preferably used according to the invention are alkyd resins with an oil content of over 45% by weight, preferably 50 to 68% by weight.

All or some of the abovementioned binder can be replaced by a fixative (mixture) or a plasticizer (mixture). These additives are intended to prevent volatilization of the active compounds and crystallization or precipitation. They preferably replace 0.01 to 30% of the binder (based on 100% of binder employed.

The plasticizers are from the chemical classes of the phthalic esters, such as dibutyl phthalate, dioctyl phthalate or benzylbutyl phthalate, the phosphoric esters, such as tributyl phosphate, the adipic esters, such as di-(2-ethylhexyl) adipate, the stearates, such as butyl stearate or amyl stearate, the oleates, such as butyl oleate, the glycerol ethers or relatively high-molecular-weight glycol ethers, glycerol esters and p-toluene-sulphonic esters.

Fixatives are chemically based on polyvinyl alkyl ethers, such as, for example, polyvinyl methyl ether, or ketones, such as benzophenone or ethylene benzophenone.

Particularly suitable as a solvent or diluent is also water, if appropriate as a mixture with one or more of the abovementioned organochemical solvents or diluents, emulsifiers and dispersants.

Particularly effective protection of wood is achieved by large-scale industrial impregnation processes, for example vacuum, double-vacuum or pressure processes.

If appropriate, the ready-to-use compositions can additionally comprise one or more other insecticides and, if appropriate, additionally one or more fungicides.

Suitable additional components which may be admixed are, preferably, the insecticides and fungicides mentioned in WO 94/29 268. The compounds mentioned in that document are expressly incorporated into the present application by reference.

Very particularly preferred components which may be admixed are insecticides, such as chlorpyriphos, phoxim, silafluofin, alphamethrin, cyfluthrin, cypermethrin, deltamethrin, permethrin, imidacloprid, NI-25, flufenoxuron, hexaflumuron and triflumuron, and fungicides, such as epoxyconazole, hexaconazole, azaconazole, propiconazole, tebuconazole, cyproconazole; metconazole, imazalil, dichlorofluanide, tolyl-fluanide, 3-iodo-2-propinylbutyl carbamate, N-octyl-isothiazolin-3-one and 4,5-di-chloro-N-octylisothiazolin-3-one.

The active compounds can be converted into the customary formulations, such as solutions, emulsions, wettable powders, suspensions, powders, dusting agents, pastes, soluble powders, granules, suspo-emulsion concentrates, natural and synthetic materials impregnated with active compound, and very fine capsules in polymeric substances.

These formulations are produced in a known manner, for example by mixing the active compounds with extenders, that is liquid solvents and/or solid carriers, optionally with the use of surfactants, that is emulsifiers and/or dispersing agents and/or foam-forming agents.

In the case of the use of water as an extender, organic solvents can, for example, also be used as auxiliary solvents. Suitable liquid solvents are essentially: aromatics, such as xylene, toluene or alkylnaphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, and also water.

Suitable solid carriers are: for example ammonium salts and ground natural minerals, such as kaolins, clays, talc, chalk, quartz, attapulgite, montmorillonite, OF diatomaceous earth, and ground synthetic minerals, such as highly disperse silica alumina and silicates, as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as protein hydrolysates; as dispersing agents there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds according to the invention can be used as such or, in their formulations, as a mixture with known herbicides for the control of weeds, in which case ready-to-use formulations or tank mixes are possible.

Suitable co-components for the mixtures are known herbicides, for example anilides such as, for example, diflufenican and propanil; arylcarboxylic acids such as, for example, dichloropicolinic acid, dicamba and picloram; aryloxyalkanoic acids such as, for example, 2,4-D, 2,4-DB, 2,4-DP, fluroxypyr, MCPA, MCPP and triclopyr; aryloxy-phenoxy-alkanoic esters such as, for example, diclofop-methyl, fenoxaprop-ethyl, fluazifop-butyl, haloxyfop-methyl and quizalofop-ethyl; azinones such as, for example, chloridazon and norflurazon, carbamates such as, for example, chlorpropham, desmedipham, phenmedipham and propham; chloroacetanilides such as, for example, alachlor, acetochlor, butachlor, metazachlor, metolachlor, pretilachlor and propachlor; dinitroanilines such as, for example, oryzalin, pendimethalin and trifluralin; diphenyl ethers such as, for example, acifluorfen, bifenox, fluoroglycofen, fomesafen, halosafen, lactofen and oxyfluorfen; ureas such as, for example, chlortoluron, diuron, fluometuron, isoproturon, linuron and methabenzthiazuron; hydroxy-lamines such as, for example, alloxydim, clethodim, cycloxydim, sethoxydim and tralkoxydim; imidazolinones such as, for example, imazethapyr, imazamethabenz, imazapyr and imazaquin; nitriles such as, for example, bromoxynil, dichlobenil and ioxynil; oxyacetamides such as, for example, mefenacet; sulphonylureas such as, for example, amido-sulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuron-methyl, triasulfuron and tribenuron-methyl; thiolcarbamates such as, for example, butylates, cycloates, di-allates, EPTC, esprocarb, molinates, prosulfocarb, thiobencarb and triallates; triazines such as, for example, atrazine, cyanazine, simazine, simetryne, terbutryne and terbutylazine; triazinones such as, for example, hexazinone, metamitron and metribuzin; others such as, for example, aminotriazole, benfuresate, bentazone, cinmethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering.

The active compounds according to the invention can be applied either before or after emergence of the plants. They can also be incorporated into the soil before sowing.

The amount of active compound used can vary within a substantial range. It depends essentially on the, nature of the desired effect. In general, the amounts used are between 1 g and 10 kg of active compound per hectare of soil surface, preferably between 5 g and 5 kg per ha.

The preparation and the use of the active compounds according to the invention can be seen from the examples below.

PREPARATION EXAMPLES

Example 1

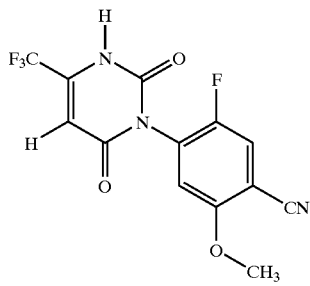

(Process (a))

A mixture of 3.8 g (12 mmol) of 1-(4-cyano-2,5-difluoro-phenyl)-3,6-dihydro-2,6-dioxo-4-trifluoromethyl-1(2H)-pyrimidine, 1.5 g (21 mmol) of sodium methoxide and 50 ml of N-methyl-pyrrolidone is stirred at 130° C. for 36 hours. After cooling of the mixture and dilution with ethyl acetate to about three times the volume, the mixture is washed with water and the product is isolated by chromatography over a silica gel column (cyclohexane/ethyl acetate, Vol.: 1/1).

1.6 g (41% of theory) of 1-(4-cyano-2-fluoro-5-methoxy-phenyl)-3,6-dihydro-2,6-dioxo-4-trifluoromethyl-1(2H)-pyrimidine of melting point 114° C. are obtained.

Example 2

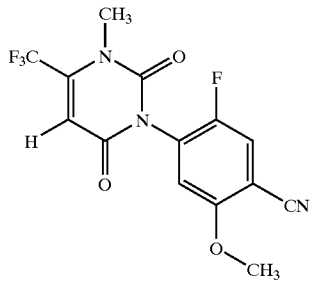

(Process (b))

A mixture of 1.5 g (4 mmol) of 1-(4-cyano-2-fluoro-5-methoxy-phenyl)-3,6-dihydro-2,6-dioxo-4-trifluoromethyl-1(2H)-pyrimidine, 0.6 g (5 mmol) of dimethyl-sulphate, 0.7 g (5 mmol) of potassium carbonate and 100 ml of acetonitrile is heated under reflux for 18 hours and then concentrated using a water pump vacuum. The residue is shaken with water/ethyl acetate and the organic phase is separated off, dried with sodium sulphate and filtered. The filtrate is concentrated using a water pump vacuum, the residue is digested with ethyl acetate/diisopropyl ether and the resulting crystalline product is isolated by filtration with suction. 1.0 g (73% of theory) of 1-(4-cyano-2-fluoro-5-methoxy-phenyl)-3,6-dihydro-2,6-dioxo-3-methyl-4-trifluoromethyl-1(2H)-pyrimidine of melting point 155° C. is obtained.

By the methods of Examples 1 and 2 and in accordance with the general description of the preparation processes according to the invention, it is also possible to prepare, for example, the compounds of the formula (I) listed in Table 1 below.

TABLE 1

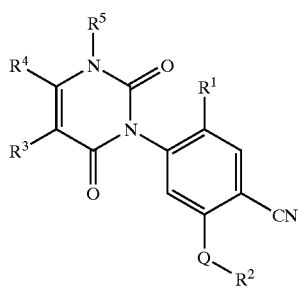

Examples of compounds of the formula (I)

| Ex. No. | Q | R¹ | R² | R³ | R⁴ | R⁵ | Melting point (° C.) |
|---|---|---|---|---|---|---|---|
| 3 | S | H | CH₂C₆H₅ | H | CF₃ | CH₃ | 88 |
| 4 | O | F | CH₂C₆H₅ | H | CF₃ | CH₃ | 45 |
| 5 | S | F | cyclopentylmethyl | H | CF₃ | CH₃ | ($n_D^{20}$ = 1.5449) |
| 6 | S | F | cyclopentylmethyl | H | CF₃ | H | 79 |
| 7 | S | F | cyclohexylmethyl | H | CF₃ | CH₃ | |
| 8 | S | F | cyclohexylmethyl | CH₃ | CH₃ | CH₃ | |
| 9 | S | F | cyclopropylmethyl | H | CF₃ | CH₃ | |
| 10 | S | F | cyclopropylmethyl | CH₃ | CF₃ | CH₃ | |
| 11 | S | F | cycloheptylmethyl | H | CF₃ | CH₃ | |
| 12 | S | F | cycloheptylmethyl | CH₃ | CF₃ | CH₃ | |
| 13 | S | F | cyclopentylmethyl | H | CF₃ | (CH₂)₃F | $n_D^{20}$ = 1.5438 |
| 14 | S | F | cyclopentylmethyl | CH₃ | CF₃ | (CH₂)₃F | |

TABLE 1-continued

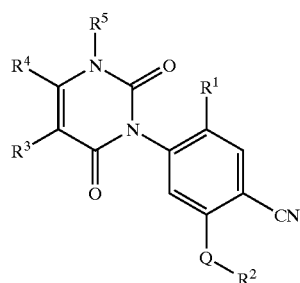

Examples of compounds of the formula (I)

| Ex. No. | Q | R¹ | R² | R³ | R⁴ | R⁵ | Melting point (° C.) |
|---|---|---|---|---|---|---|---|
| 15 | S | F | cyclopentylmethyl | H | $CH_3$ | $(CH_2)_3F$ | |
| 16 | S | F | cyclopentylmethyl | $CH_3$ | $CH_3$ | $(CH_2)_3F$ | |
| 17 | O | F | $CH_2C{\equiv}CH$ | H | $CF_3$ | $CH_3$ | 145 |
| 18 | O | F | $CH_2C{\equiv}CH$ | H | $CF_3$ | $C_2H_5$ | |
| 19 | O | F | $CH(CH_3)C{\equiv}CH$ | H | $CF_3$ | $CH_3$ | 115 |
| 20 | O | F | $CH(CH_3)C{\equiv}CH$ | H | $CF_3$ | $C_2H_5$ | |
| 21 | O | H | $CH_2C{\equiv}CH$ | H | $CF_3$ | $CH_3$ | |
| 22 | O | H | $CH(CH_3)C{\equiv}CH$ | H | $CF_3$ | $CH_3$ | |
| 23 | O | F | $CH_2CH{=}CH_2$ | H | $CF_3$ | $CH_3$ | 157 |
| 24 | O | F | $CH(CH_3)CH{=}CH_2$ | H | $CF_3$ | $CH_3$ | |
| 25 | O | F | $CH_2CH_2COOCH_3$ | H | $CF_3$ | $CH_3$ | >200 |
| 26 | O | F | $CH_2CH_2COOC_2H_5$ | H | $CF_3$ | $CH_3$ | |
| 27 | O | F | $CH(CH_3)COOCH_3$ | H | $CF_3$ | $CH_3$ | |

TABLE 1-continued

Examples of compounds of the formula (I)

| Ex. No. | Q | R¹ | R² | R³ | R⁴ | R⁵ | Melting point (° C.) |
|---|---|---|---|---|---|---|---|
| 28 | O | F | -CH(CH₃)-COOC₂H₅ | H | CF₃ | CH₃ | |
| 29 | O | F | -CH₂-COOH | H | CF₃ | CH₃ | |
| 30 | O | F | -CH(CH₃)-COOH | H | CF₃ | CH₃ | |
| 31 | O | F | C₂H₅ | H | CF₃ | H | 123 |
| 32 | O | F | C₂H₅ | H | CF₃ | CH₃ | 121 |
| 33 | O | F | CH₃ | H | CF₃ | C₂H₅ | 90 |
| 34 | O | F | -CH₂-C(O)-OCH₃ | H | CF₃ | H | 185 |
| 35 | O | F | -CH₂-C(O)-N(CH(CH₃)₂)(4-F-C₆H₄) | H | CF₃ | CH₃ | >200 |
| 36 | O | F | -CH₂-C(O)-N(C₂H₅)₂ | H | CF₃ | CH₃ | 1H-NMR (CDCl₃, δ): 6.33 ppm(s, 1H) |
| 37 | O | F | -CH₂-C≡CH | H | CF₃ | H | 140 |
| 38 | O | F | -CH₂-CH=CH₂ | H | CF₃ | H | |
| 39 | O | F | -CH(CH₃)-C≡CH | H | CF₃ | H | 202 |
| 40 | O | F | C₂H₅ | H | CF₃ | CHF₂ | 177 |

TABLE 1-continued

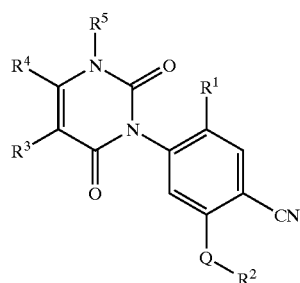

Examples of compounds of the formula (I)

| Ex. No. | Q | $R^1$ | $R^2$ | $R^3$ | $R^4$ | $R^5$ | Melting point (° C.) |
|---|---|---|---|---|---|---|---|
| 41 | O | F | cyclopentyl-CH2 | H | $CF_3$ | H | 200 |
| 42 | O | F | cyclopentyl-CH2 | H | $CF_3$ | $CH_3$ | |
| 43 | O | F | cyclohexyl-CH2 | H | $CF_3$ | H | 221 |
| 44 | O | F | oxetan-CH2 | H | $CF_3$ | H | 130 |
| 45 | O | F | cyclohexyl-CH2 | H | $CF_3$ | $CH_3$ | |
| 46 | O | F | oxetan-CH2 | H | $CF_3$ | $CH_3$ | |
| 47 | S | F | cyclopentyl-CH2 | $CH_3$ | $CF_3$ | $CH_3$ | $n_D^{20} = 1.5628$ |
| 48 | O | F | $-CH_2-C(O)-N(C_2H_5)_2$ | H | $CF_3$ | H | 88 |

Use Examples

Example A

Pre-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Seeds of the test plants are sown in normal soil. After 24 hours, the soil is watered or sprayed with the preparation of the active compound. It is advantageous to keep the amount of water per unit area constant. The concentration of the active compound in the preparation is immaterial, only the amount of active compound applied per unit area matters.

After three weeks, the degree of damage to the plants is rated in % damage by comparison with the development of the untreated control.

The Figures Denote

0%=no effect (like untreated control)

100%=total destruction

In this test, very strong activity against weeds such as Digitaria (90–100%), Setaria (95–100%), Abutilon (100%), Chenopodium (100%/o) and Matricaria (100%/o) is shown, for example, by the compounds of Preparation Examples 2 and 4 at application rates between 8 and 125 g/ha, combined with good tolerance by crops such as, for example, wheat (0%).

Example B

Post-emergence Test

Solvent: 5 parts by weight of acetone

Emulsifier: 1 part by weight of alkylaryl polyglycol ether

To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is chosen so that the particular desired amounts of active compound are applied in 2000 l of water/ha.

After three weeks, the degree of damage to the plants is rated in % damage by comparison with the development of the untreated control.

The Figures Denote

0%=no effect (like untreated control)

100%=total destruction

In this test, very strong activity against weeds such as Panicum (95–100%), Setaria (90–100%), Sorghum (80–95%), Abutilon (100%), Chenopodium (100%) and Matricaria (100%) is shown, for example, by the compounds of Preparation Examples 2 and 4 at application rates between 30 and 500 g/ha.

Example C

Phaedon Larvae Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration. Cabbage leaves (*Brassica oleracea*) are treated by being dipped into the preparation of the active compound of the desired concentration and are infested with mustard beetle larvae (*Phaedon cochleariae*) while the leaves are still moist.

After the desired period of time, the destruction in % is determined. 100% means that all the beetle larvae have been killed; 0% means that none of the beetle larvae have been killed.

In this test, a destruction of 100% was caused, after 7 days, for example by the compound of Preparation Example 4 at an exemplary active compound concentration of 0.1%.

Example D

Plutella Test

Solvent: 7 parts by weight of dimethylformamide

Emulsifier: 1 part by weight of alkylaryl polyglycol ether

To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with caterpillars of the diamond-back moth (*Plutella maculipennis*) while the leaves are still moist.

After the desired period of time, the destruction in % is determined. 100% means that all the caterpillars have been destroyed; 0% means that none of the caterpillars have been destroyed.

In this test, a destruction of 100% was caused, after 7 days, for example by the compound of preparation example 4 at an exemplary active compound concentration of 0.1%.

What is claimed is:

1. A compound of the formula (I)

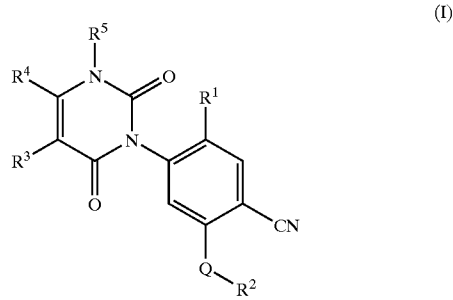

wherein

Q represents O, SO or $SO_2$, $R^1$ represents hydrogen, cyano, fluorine or chlorine, $R^2$ represents aryl having 6 or 10 carbon atoms in the aryl moiety optionally substituted with cyano, carboxyl, nitro, carbamoyl, thiocarbamoyl, fluorine, chlorine, bromine, $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl or $C_1$–$C_4$-alkoxy-carbonyl (wherein each $C_1$–$C_4$ moiety is optionally substituted by fluorine and/or chlorine), phenyl, phenoxy or phenylthio (wherein each phenyl, phenoxy or phenylthio moiety is optionally substituted by fluorine, chlorine, bromine, cyano, methyl, methoxy, trifluoromethyl and/or trifluoromethoxy), or $R^2$ represents furyl, tetrahydrofuryl, thienyl, tetrahydrothienyl, oxetanyl, thietanyl, oxazolyl, isoxazolyl, thiazolyl, oxadiazolyl, thiadiazolyl, pyrazolyl, pyridinyl, pyrimidinyl, triazinyl, indolyl, quinolinyl or quinoxalinyl, wherein each heterocyclic moiety is optionally substituted with cyano, carboxyl, carbamoyl, thiocarbamoyl, fluorine, chlorine, bromine, $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl or $C_1$–$C_4$-alkoxy-carbonyl (wherein each $C_1$–$C_4$ moiety is optionally substituted by fluorine and/or chlorine), or phenyl, phenoxy or phenylthio (wherein each phenyl, phenoxy or phenylthio moiety is optionally substituted by fluorine, chlorine, bromine, cyano, methyl, methoxy, trifluoromethyl and/or trifluoromethoxy), $R^3$ represents hydrogen, fluorine, chlorine, bromine or represents respectively optionally fluorine- and/or chlorine-substituted alkyl or alkoxy having in each case 1 to 4 carbon atoms, $R^4$ represents optionally fluorine- and/or chlorine-substituted alkyl having 1 to 4 carbon atoms and $R^5$ represents hydrogen or represents respectively optionally fluorine-, chlorine- or $C_1$–$C_4$-alkoxy-substituted alkyl, alkoxy, alkenyl or alkinyl having in each case up to 6 carbon atoms.

2. The compound of the formula (I) according to claim 1, wherein

Q represents O, SO or $SO_2$, $R^1$ represents hydrogen, fluorine or chlorine, $R^2$ represents phenyl optionally substituted with cyano, carboxyl, nitro, carbamoyl, thiocarbamoyl, fluorine, chlorine, bromine, methyl, ethyl, n- or i-propyl, n-, i-, s- or t-butyl, trifluoro-methyl, methoxy, ethoxy, n- or i-propoxy, methylthio, ethylthio, methylsulphinyl, ethylsulphinyl, methylsulphonyl, ethylsulphonyl, acetyl, propionyl, methoxycarbonyl, ethoxycarbonyl, n- or i-propoxycarbonyl, or $R^2$ represents furyl, tetrahydrofuryl, thienyl, tetrahydrothienyl, oxetanyl, thietanyl, oxazolyl, isoxazolyl, thiazolyl, oxadiazolyl, thiadiazolyl, pyrazolyl, pyridinyl, pyrimidinyl, triazinyl, indolyl, quinolinyl or quinoxalinyl, wherein each heterocyclic moiety is optionally substituted with cyano, carboxyl, carbamoyl, thiocarbamoyl, fluorine, chlorine, bromine, methyl, ethyl, n- or i-propyl, methoxy, ethoxy, n- or i-propoxy, methylthio, ethylthio, methylsulphinyl, ethylsulphinyl, methylsulphonyl, ethylsulphonyl, acetyl, propionyl, methoxycarbonyl, ethoxycarbonyl, n- or i-propoxycarbonyl, phenyl, phenoxy or phenylthio, $R^3$ represents hydrogen, fluorine, chlorine, bromine or methyl, $R^4$ represents methyl, ethyl, difluoromethyl, dichloromethyl, trifluoromethyl, trichloromethyl, chlorodifluoromethyl, fluorodichloromethyl, chloroethyl, fluoroethyl, dichloroethyl, dichloroethyl, chlorofluoroethyl, chlorodifluoroethyl, fluorodichloroethyl, trifluoroethyl, tetrafluoroethyl, chlorotrifluoroethyl or pentafluoroethyl and $R^5$ represents hydrogen or represents respectively optionally fluorine-, chlorine-, methoxy- or ethoxy-substituted methyl, ethyl, n- or i-propyl, n-, i-, s- or t-butyl, methoxy, ethoxy, n- or i-propoxy, n-, i- or s-butoxy, propenyl, butenyl, propinyl or butinyl.

3. The compound of claim 1 wherein, $R^2$ represents aryl having 6 or 10 carbon atoms in the aryl moiety optionally substituted with cyano, carboxyl, nitro, carbamoyl, thiocarbamoyl, fluorine, chlorine, bromine, $C_1$–$C_4$alkyl, $C_1$–$C_4$-alkoxy, $C_1$–$C_4$-alkylthio, $C_1$–$C_4$-alkylsulphinyl, $C_1$–$C_4$-alkylsulphonyl, $C_1$–$C_4$-alkyl-carbonyl or $C_1$–$C_4$-alkoxy-carbonyl (wherein each $C_1$–$C_4$ moiety is optionally substituted by fluorine and/or chlorine), phenyl, phenoxy or phenylthio (wherein each phenyl, phenoxy or phenylthio moiety is optionally substituted by fluorine, chlorine, bromine, cyano, methyl, methoxy, trifluoromethyl and/or trifluoromethoxy).

4. The compound of claim 1 wherein, $R^2$ represents furyl, tetrahydrofuryl, thienyl, tetrahydrothienyl, oxetanyl, thietanyl, oxazolyl, isoxazolyl, thiazolyl, oxadiazolyl, thiadiazolyl, pyrazolyl, pyridinyl, pyrimidinyl, triazinyl, indolyl, quinolinyl or quinoxalinyl, wherein each heterocyclic moiety is optionally substituted with cyano, carboxyl, carbamoyl, thiocarbamoyl, fluorine, chlorine, bromine, $C_1$–$C_4$-alkyl, $C_1$–$C_4$-alkoxy, $C_1$–$C_4$-alkylthio, $C_1$–$C_1$–$C_4$ alkylsulphinyl, $C_1$–$C_4$-alkylsulphonyl, $C_1C_4$-alkyl-carbonyl or $C_1$–$C_4$-alkoxy-carbonyl (wherein each $C_1$–$C_4$ moiety is optionally substituted by fluorine and/or chlorine), or phenyl, phenoxy or phenylthio (wherein each phenyl, phenoxy or phenylthio moiety is optionally substituted by fluorine, chlorine, bromine, cyano, methyl, methoxy, trifluoromethyl and/or trifluoromethoxy).

5. A compound of the formula (1a)

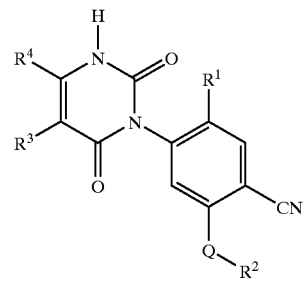

(Ia)

wherein

Q, $R^1$, $R^2$, $R^3$ and $R^4$ are each as defined in claim 1.

6. An herbicidal composition comprising an herbicidally effective amount of a compound according to claim 1 and a diluent.

7. A method of controlling unwanted vegetation which comprises applying to such vegetation or to a locus from which it is desired to exclude such vegetation an herbicidally effective amount of a compound according to claim 1.

* * * * *

UNITED STATES PATENT AND TRADEMARK OFFICE
CERTIFICATE OF CORRECTION

PATENT NO.   : 6,495,491 B1
DATED        : December 17, 2002
INVENTOR(S)  : Roland Andree et al.

It is certified that error appears in the above-identified patent and that said Letters Patent is hereby corrected as shown below:

<u>Column 36,</u>
Line 15, change "$C_1$-$C_1$-$C_4$ alkylsulphinyl" to -- $C_1$-$C_4$ alkylsulphinyl --

Signed and Sealed this

Seventeenth Day of June, 2003

JAMES E. ROGAN
*Director of the United States Patent and Trademark Office*